US012064522B2

(12) United States Patent
Wang et al.

(10) Patent No.: US 12,064,522 B2
(45) Date of Patent: Aug. 20, 2024

(54) LOW TEMPERATURE PROCESS FOR PREPARING SILICON OXIDE COATED PHARMACEUTICALS

(71) Applicant: Applied Materials, Inc., Santa Clara, CA (US)

(72) Inventors: Fei Wang, Fremont, CA (US); Miaojun Wang, Santa Clara, CA (US); Colin C. Neikirk, Mountain View, CA (US); Jonathan Frankel, Los Gatos, CA (US); Pravin K. Narwankar, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 12 days.

(21) Appl. No.: 17/492,363

(22) Filed: Oct. 1, 2021

(65) Prior Publication Data

US 2022/0105048 A1     Apr. 7, 2022

Related U.S. Application Data

(60) Provisional application No. 63/087,040, filed on Oct. 2, 2020.

(51) Int. Cl.
*A61K 9/50*     (2006.01)
(52) U.S. Cl.
CPC .......... *A61K 9/5089* (2013.01); *A61K 9/501* (2013.01)
(58) Field of Classification Search
CPC .... A61K 9/5089; A61K 9/501; A61K 9/5115; A61K 31/506; A61P 25/36
See application file for complete search history.

(56) References Cited

U.S. PATENT DOCUMENTS

| | | | |
|---|---|---|---|
| 4,289,871 A | 9/1981 | Rowan et al. |
| 6,165,512 A | 12/2000 | Mezaache et al. |
| 6,613,383 B1 | 9/2003 | George et al. |
| 7,357,910 B2 | 4/2008 | Phillips et al. |
| 8,524,772 B2 | 9/2013 | Arad et al. |
| 8,697,097 B2 | 4/2014 | Nonomura et al. |
| 10,166,198 B2 | 1/2019 | Carlsson et al. |
| 10,512,796 B2 | 12/2019 | Toledano et al. |
| 10,603,284 B2 | 3/2020 | Hoppu et al. |
| 11,041,238 B2 | 6/2021 | Arl et al. |

(Continued)

FOREIGN PATENT DOCUMENTS

| | | |
|---|---|---|
| CN | 111712235 | 9/2020 |
| DE | 10307568 | 9/2004 |

(Continued)

OTHER PUBLICATIONS

"Pharmaceutical Preparations," European Pharmacopoeia 8.0, Apr. 2013, 756-758.

(Continued)

*Primary Examiner* — Dah-Wei D. Yuan
*Assistant Examiner* — Andrew J Bowman
(74) *Attorney, Agent, or Firm* — Fish & Richardson P.C.

(57) ABSTRACT

A method of preparing a pharmaceutical composition having a drug-containing core enclosed by one or more silicon oxide materials is provided. The method entails alternating exposing the particles to gaseous or vaporous $SiCl_4$ and gaseous or vaporous $H_2O$ at a reduced temperature and in the absence of a catalyst.

32 Claims, 5 Drawing Sheets

(56) References Cited

U.S. PATENT DOCUMENTS

| | | | |
|---|---|---|---|
| 2003/0026989 A1 | 2/2003 | George et al. | |
| 2003/0118642 A1 | 6/2003 | Norman et al. | |
| 2004/0037883 A1 | 2/2004 | Zhou et al. | |
| 2005/0266078 A1 | 12/2005 | Jorda et al. | |
| 2006/0263479 A1 | 11/2006 | Boghani et al. | |
| 2007/0036850 A1 | 2/2007 | Roehrich et al. | |
| 2007/0280895 A1 | 12/2007 | Weimer et al. | |
| 2008/0069891 A1* | 3/2008 | Habib | A61P 25/36 424/490 |
| 2009/0186968 A1 | 7/2009 | Zong et al. | |
| 2010/0136110 A1 | 6/2010 | Tasaki et al. | |
| 2010/0297251 A1 | 11/2010 | Timmons et al. | |
| 2010/0303722 A1 | 12/2010 | Jin et al. | |
| 2011/0091563 A1 | 4/2011 | Kurasawa et al. | |
| 2011/0300224 A1 | 12/2011 | Murpani et al. | |
| 2012/0201860 A1 | 8/2012 | Weimer et al. | |
| 2013/0336866 A1 | 12/2013 | Soeger et al. | |
| 2013/0337056 A1 | 12/2013 | Lehtonen et al. | |
| 2015/0250731 A1 | 9/2015 | Hoppu et al. | |
| 2016/0081945 A1* | 3/2016 | Carlsson | A61K 9/5115 424/490 |
| 2017/0007545 A1 | 1/2017 | Hoppu et al. | |
| 2019/0216742 A1* | 7/2019 | Neikirk | A61K 31/506 |
| 2020/0197313 A1 | 6/2020 | Hoppu et al. | |

FOREIGN PATENT DOCUMENTS

| | | |
|---|---|---|
| EP | 1621187 | 2/2006 |
| JP | 2004-269384 | 9/2004 |
| JP | 2005-060309 | 3/2005 |
| JP | 2005-520796 | 7/2005 |
| JP | 2008-013480 | 1/2008 |
| JP | 2008-539801 | 11/2008 |
| JP | 2010-501538 | 1/2010 |
| JP | 2011-063627 | 3/2011 |
| JP | 2012-051810 | 3/2012 |
| JP | 2014-510066 | 4/2014 |
| JP | 2015-528487 | 9/2015 |
| JP | 2016-519155 | 6/2016 |
| KR | 10-2016-0090478 | 8/2016 |
| WO | WO 1990/002546 | 3/1990 |
| WO | WO 2006/090640 | 8/2006 |
| WO | WO 2007/015243 | 2/2007 |
| WO | WO 2008/023184 | 2/2008 |
| WO | WO 2010/135107 | 11/2010 |
| WO | WO 2011/011207 | 1/2011 |
| WO | WO 2011/141486 | 11/2011 |
| WO | WO 2012/116814 | 9/2012 |
| WO | WO 2019/143744 | 7/2019 |
| WO | WO 2019/241351 | 12/2019 |

OTHER PUBLICATIONS

Andrew et al., "Sustained Release of a Monoclonal Antibody from Electrochemically Prepared Mesoporous Silicon Oxide," Advanced Functional Materials, Dec. 2010, 20(23):4168-4174.

Arin et al., "Characterization of ZnO—TiO2 and zinc titanate nanoparticles synthesized by hydrothermal process," Res Chem Intermed, 2017, 43:3183-3195.

Arl et al., "SiO2 thin film growth through a pure atomic layer deposition technique at room temperature," Royal Society of Chemistry, May 2020, 10:18073-18081.

Groner et al., "Low-temperature Al2O3 atomic layer deposition," Chemistry of Materials, Chemistry of Materials, American Chemical Society, US, Feb. 24, 2004, 16(4):639-645.

International Search Report and Written Opinion in International Application No. PCT/US2021/053223, dated Jan. 24, 2022, 10 pages.

Kaariainen et al., "Surface modification of acetaminophen particles by atomic layer deposition," International Journal of Pharmaceutics, Apr. 18, 2017, 525(1):160-174.

Klaus et al., "SiO2 Chemical Vapor Deposition at Room Temperature Using SiCl4 and H 2 O with an NH 3 Catalyst," Journal of the Electrochemical Society, 2000, 147(7):2658-2664.

Knez et al., "Synthesis and Surface Engineering of Complex Nanostructures by Atomic Layer Deposition," Advanced Materials, Nov. 5, 2007, 19(21):3425-3438.

Knez et al., "Atomic Layer Deposition on Biological Macromolecules: Metal Oxide Coating of Tobacco Mosaic Virus and Ferritin," Nano Letters, 2006, 6(6):1172-1177.

Martino et al., "A new pure paracetamol for direct compression: The orthorhombic form," International Journal of Pharmaceutics, 1996, 128:1-8.

Patel et al., "Ensuring Better Control of Granulation," Pharmaceutical Manufacturing, Aug. 7, 2008, http://www.pharmamanufacturing/com/articles/2008/096/, 11 pages.

Prescott et al., "On Powder Flowability," Pharmaceutical Technology, Oct. 2000, 14 pages.

Shah et al., "Comparative Evaluation of Flow for Pharmaceutical Powders and Granules," AAPS PharmSciTech, 2008, 9(1):250-258.

Siddiqi et al., "Properties of Zinc Oxide Nanoparticles and Their Activity Against Microbes," Nanoscale Research Letters, 2018, 13:141, 13 pages.

Singh et al., "Microencapsulation: A promising technique for controlled drug delivery," Res. Pharnn. Sci., 2010, 5(2):65-77.

Verheezen et al., "Milling of agglomerates in an impact mill," Int. J. Pharm., 2004, 278:165-172.

Wikipedia.com [online], "Titanium Oxide," retrieved on Aug. 20, 2021, retrieved from URL <https://en.wikipedia.org/wiki/Titanium_oxide>, 1 page.

Wu et al., "Preparation and properties of composite particles made by nano zinc oxide coated with titanium dioxide," J. Mater. Sci., 2006, 41:5845-5850.

Www.ahdictionary.com [online], "Granule," retrieved on Aug. 9, 2019, retrieved from URL <https:www.ahdictionary.com/word/search/html?q=granule>, 3 pages.

Xie et al., "Atomic layer deposition of TiO2 from tetrakis-dimethyl-amido titanium or Ti isopropoxide precursors and H2O," Journal of Applied Physics, 2007, 102:7 pages.

Guo et al., "Room-temperature pulsed CVD grown SiO2 protective layer on TiO2 particles for photocatalytic activity suppression" RSC advances, Jan. 16, 2017, p. 4547-4554.

Avssymposium.org [online], "ALD2020 Session AA1-MoA: Emerging Applications of ALD I & II, AAI-MoA-7 Understanding and Controlling Release and Aerosolization of Inhaled Drug Particles Engineered by Atomic Layer Deposition," Jun. 29, 2020, retrieved on Nov. 17, 2022, retrieved from URL<https://www.avssymposium.org/ALD2020/Sessions/Schedule/58315>, 3 pages.

Office Action in Indian Appln. No. 202347029740, dated Jul. 24, 2023, 7 pages.

* cited by examiner

LOW TEMPERATURE PROCESS FOR PREPARING SILICON OXIDE COATED PHARMACEUTICALS

CROSS-REFERENCE TO RELATED APPLICATIONS

This application claims priority to U.S. Provisional Patent Application Ser. No. 63/087,040, filed on Oct. 2, 2020, the disclosure of which is incorporated by reference.

TECHNICAL FIELD

This disclosure pertains to coated drug compositions and methods of preparing coated drug compositions.

BACKGROUND

It is of great interest to the pharmaceutical industry to develop improved formulations of active pharmaceutical ingredients (APIs). Formulation can influence the stability and bioavailability of APIs as well as other characteristics. Formulation can also influence various aspects of drug product (DP) manufacture, for example, ease and safety of the manufacturing process.

Many APIs used to prepare DPs are cohesive particles that have poor flowability and readily agglomerate. Excipients, for example, silica, are often added to API particles to improve flowability and other handling characteristics.

Numerous technologies for encapsulating or coating both APIs and DPs have been developed, e.g., polymer mesh coating, pan coating, aerosolized coating, fluidized bed reactor coating, molecular layer deposition coating, and atomic layer deposition coating.

SUMMARY

In one aspect, a method of preparing coated particles having an active pharmaceutical ingredient (API)-containing core enclosed by one or more silicon oxide ($SiO_2$) layers is disclosed. The silicon oxide layer is deposited using a relatively low temperature process (i.e., the temperature of the particles does not exceed 100° C. and is preferably between 20° C. and 40° C. during the entire deposition process) without the use of a catalyst, e.g., without the use of an amine catalyst. The silicon oxide coating is conformal and pin-hole free. The process can be used to coat particles that consist of APIs; particles that comprise one or more APIs and one or more excipients; and particles that consist of APIs and one more excipients, for example, particles of an amorphous solid dispersion of one or more APIs and one or more excipients. After the silicon oxide layer is deposited, a polymer layer can be applied by molecular layer deposition (MLD) or hybrid ALD/MLD deposition. These steps can be repeated to create particles having an API-containing core enclosed by multiple layers (e.g., multiple alternating layers) of silicon oxide and polymer.

The silicon oxide layer is thin and conforms to the API-containing core. This layer can greatly improve the flowability and other handling characteristics of the API-containing core. The coating layer can adjust the dissolution rate of the API, such as for extended release coating, an enteric coating and can increase the stability of the API, e.g., can increase resistance to oxidation and/or alteration in crystalline form. Thus, the coating layers can reduce transition of the API form an amorphous form to a crystalline form. The coating layers can provide bulking and/or improve compressibility thereby reducing the need for excipients. By reducing the need for additional excipients, the coated particles can be used to create dosage forms with high drug loading.

Described herein is a composition comprising individual particles comprising an API-containing core (e.g., a core consisting of an API or an API and one or more excipients) enclosed by an silicon oxide layer, wherein the core has a median particle size, on a volume average basis, between 0.1 µm and 40 µm, and the silicon oxide layer has an average thickness of 5 nm to 100 nm.

In various embodiments, the temperature of the interior of the reactor does not exceed 50° C., 40° C., 35° C.; is 50° C.-30° C.; or is 45° C.-20° C. or is 25° C.-50° C.

Described herein is a method of preparing coated particles comprising an active pharmaceutical ingredient (API)-containing core enclosed by one or more silicon oxide layers, the method comprising:

(a1) loading core particles comprising an API into a reactor;
(a2) applying gaseous $SiCl_4$ to the core particles in the reactor;
(a3) performing one or more pump-purge cycles of the reactor using inert gas;
(a4) applying gaseous $H_2O$ to the core particles in the reactor;
(a5) lowering the gaseous $H_2O$ in the reactor to below 0.5 Torr; and
(a6) optionally performing one or more pump-purge cycles of the reactor using inert gas, wherein steps (a2)-(a6) take place between 25° C. and 50° C. and in the absence of a catalyst.

In various embodiments: step (a6) is not performed; step (a6) is performed; steps (a2)-(a6) are performed two or more times to increase the total thickness of the silicon oxide layer; the reactor contents are agitated prior to and/or during one or more of steps (a2) to (a6); the reactor pressure is allowed to stabilize following step (a1), step (a2), and/or step (a4); the reactor contents are agitated prior to and/or during step (a1), step (a3), and/or step (a5); a subset (e.g., some, but not all) of vapor or gaseous content is pumped out prior to step (a3) and/or step (a5); the silicon oxide layer has a thickness in a range of 0.1 nm to 50 nm; steps (a2)-(a6) are repeated two or more times and the core particles are not removed from the reactor between each repetition; steps (a2)-(a6) are repeated two or more times and the particles are not removed from the reactor during step until the silicon oxide layer is complete; the core particles comprising an API further comprise one or more pharmaceutically acceptable excipients; the core particles consist of API; the core particles comprising an API have a median particle size, on a volume average basis between 0.1 µm and 20 µm prior to step (a1); the core particles have a median particle size, on a volume average basis between 0.1 µm and 5 µm prior to step (a1); the core particles have a median particle size, on a volume average basis between 0.1 µm and 1000 µm prior to step (a1); the core particles comprise a first API and a second API; the core particles consist of an API; the core particles consist of a first API and a second API; the core particles comprise an API and one or more pharmaceutically acceptable excipients; the core particles comprise a first API, a second API and one or more pharmaceutically acceptable excipients; the particles remain in the reactor until the coating is complete; the core particles consist of an API and one or more pharmaceutically acceptable excipients; and core particles consist of a first API, a second API and one or more pharmaceutically acceptable excipients.

Moreover, one or more of the gases (e.g., water vapor and/or gaseous $SiCl_4$ and/or the inert gas) can be supplied in pulses in which the chamber is filled with the gas to a specified pressure, a holding time is permitted to pass (e.g., as short as 1 sec or as long as, e.g., one hour), and the chamber is evacuated to some extent by the vacuum pump before the next pulse commences. Thus, each of steps (a2), (a3), (a4) and (a6) can comprises multiple pulses.

In various embodiments: step (a1) further comprises one or both of loading particles comprising a second API into the reactor (second core particles) and loading particles comprising one more excipients into the reactor (excipient particles); the method further comprises admixing the coated particles comprising an API-containing core enclosed by one or more silicon oxide layers with a pharmaceutically acceptable diluent or carrier; and the method further comprises processing the coated particles comprising an API-containing core enclosed by one or more silicon oxide layers to form a tablet or capsule; and the method further comprises admixing the coated particles comprising an API-containing core enclosed by one or more silicon oxide layers with a pharmaceutically acceptable diluent or carrier to form a mixture and processing the mixture to form a table or capsule.

In some embodiments, the silicon oxide layer on the coated particles has a thickness in the range of 0.1 nm to 120 nm.

In some embodiments, the silicon oxide layer on the coated particles has a thickness in the range of 50 nm to 120 nm.

In some embodiments, the silicon oxide layer has a thickness in range of 0.1 nm to 100 nm or 0.1 nm to 10 nm or 0.1 nm to 50 nm.

The in some embodiments the API is suitable for oral administration.

In some embodiments, the API and/or the uncoated particles comprising an API do not comprise a metal oxide, do not comprise silicon oxide, and/or do not comprise aluminum oxide.

In some embodiments, the uncoated particles are at least 50% wt/wt API. In some embodiments, the uncoated particles are at least 70%, 80%, 90%, 99% or 100% wt/wt API. In some cases, the API is crystalline. In some embodiments, the coated particles have a D50 of 0.1 μm to 200 μm or 0.1 μm to 1 μm or 0.1 μm to 10 μm 0.1 μm to 50 μm on a volume average basis. In some embodiments, the coated particles have a D90 of 200 μm to 2000 μm on a volume average basis. In some embodiments, the uncoated particles have a D50 of 0.1 μm to 200 μm or 0.1 μm to 1 μm or 0.1 μm to 10 μm 0.1 μm to 50 μm on a volume average basis. In some embodiments, the uncoated particles have a D90 of 200 μm to 2000 μm on a volume average basis.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

Other features and advantages of the invention will be apparent from the following detailed description and figures, and from the claims.

DETAILED DESCRIPTION

Figure 1:
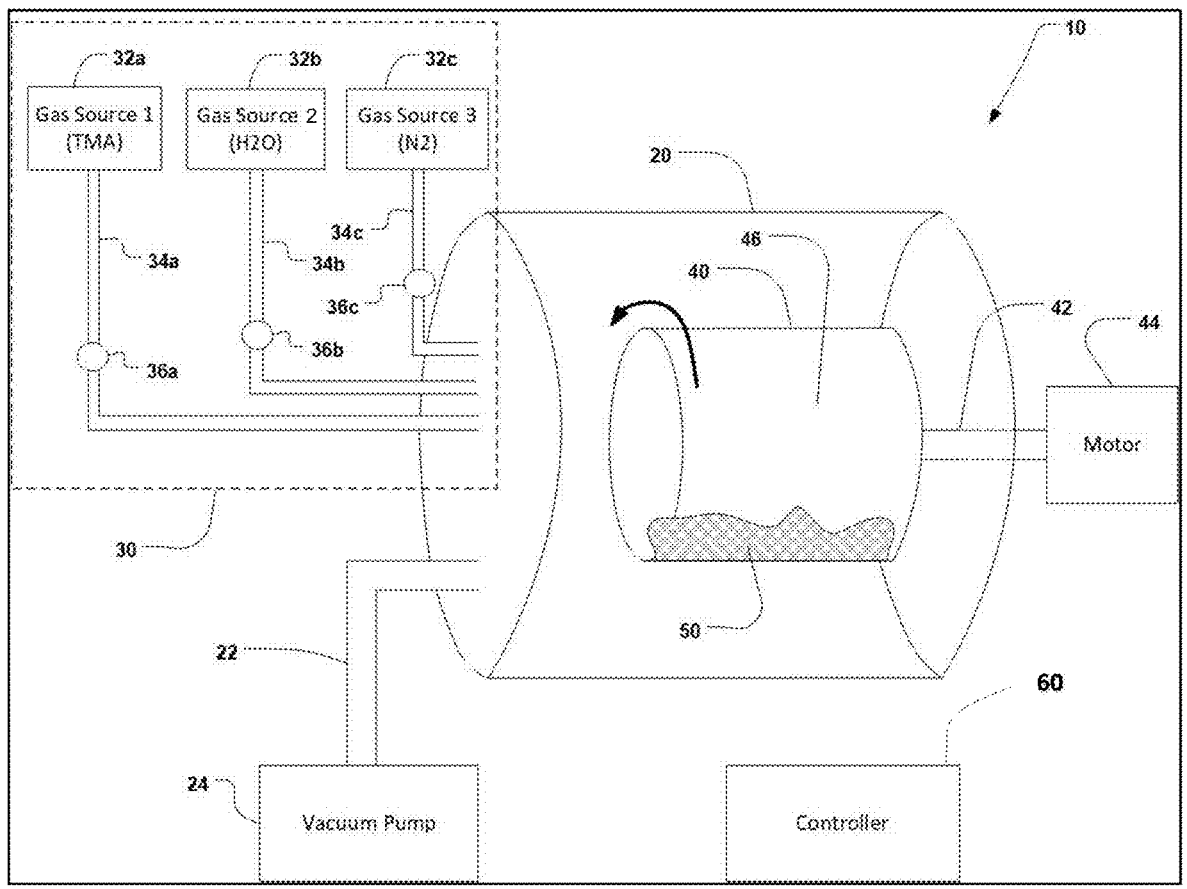
FIG. 1 is a schematic illustration of a rotary reactor for coating of particles, e.g., particles comprising an API.

There are various methods for providing a silicon oxide coating to an object by chemical vapor deposition or atomic layer deposition. Many of these processes require processing at an elevated temperature and/or the presence of a catalyst, for example, a Lewis base. Described herein is a method for applying a silicon oxide coating to particles comprising an API that does not entail the use of an elevated temperature or a catalyst. Instead, proper control of precursor ($SiCl_4$) and oxidant ($H_2O$) vapor pressure, hold time and the use of purging are used to create a conformal, pinhole coating.

The present disclosure provides methods of preparing pharmaceutical compositions comprising API (drug) containing particles encapsulated by one or more layers of silicon oxide. The coating layers are conformal and have a thickness of 1-50 nanometers. The particles to be coated can be composed of only APIs or a combination of APIs and one or more excipients. The coating process described herein can provide an API with an increased glass transition temperature for the API relative to an uncoated API, a decreased rate of crystallization for an amorphous form of the API relative to an uncoated API, and decreased surface mobility of API molecules in the particle compared to uncoated APIs. Importantly, API particle dissolution can be altered. Because the coating is relatively thin, drug products with high drug loading can be achieved.

The term "drug" in its broadest sense includes all small molecule (e.g., non-biologic) APIs. The drug could be selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

Exemplary types of small molecule drugs include, but are not limited to, acetaminophen, clarithromycin, azithromycin, ibuprofen, metformin, theophylline, fluticasone propionate, salmeterol, pazopanib HCl, palbociclib, and amoxicillin potassium clavulanate.

Atomic layer deposition (ALD) (alternatively referred to as atomic layer coating (ALC)) is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Chemical vapor deposition (CVD), like ALD, is deposition technique that uses a gaseous precursor and a gaseous oxidant. However, the process is more continuous than ALD because the precursor and the oxidant can be present at the same time.

The term "reactor system" in its broadest sense includes all systems that could be used to perform ALD or mixed ALD/CVD or CVD. An exemplary reactor system is illustrated in FIG. 1 and further described below in the context of an ALD reaction. The same or a similar reactor system can be used to perform MLD, hybrid MLD/ALD.

FIG. 1 illustrates a reactor system 10 for performing coating of particles, with thin-film coatings. The reactor system 10 can perform the coating using ALD and/or hybrid, and/or MLD coating conditions. The reactor system 10 permits a coating process (ALD or MLD or hybrid), to be performed at a higher (above 50° C., e.g., 50-100° C.) or lower processing temperature, e.g., below 50° C., e.g., at or below 35° C. For example, the reactor system 10 can form thin-film silicon oxides on the particles. In general, the particles can remain or be maintained within a desired temperature range. This can be achieved by having the reactant gases and/or the interior surfaces of the reactor chamber (e.g., the chamber 20 and drum 40 discussed below) remain or be maintained at such temperatures.

As an example, the reactor system 10 includes a stationary vacuum chamber 20 which is coupled to a vacuum pump 24 by vacuum tubing 22. The vacuum pump 24 can be an industrial vacuum pump sufficient to establish pressures less than 1 Torr, e.g., 1 to 100 mTorr, e.g., 50 mTorr. The vacuum pump 24 permits the chamber 20 to be maintained at a desired pressure, and permits removal of reaction byproducts and unreacted process gases.

In operation, the reactor 10 performs the thin-film coating process by introducing gaseous precursors of the coating into the chamber 20. The gaseous precursors are spiked alternatively into the reactor. This permits the process to be a solvent-free process. The half-reactions of the process are self-limiting, surface reactions, which can provide Angstrom level control of deposition. In addition, the reaction can be performed at low temperature conditions, such as below 50° C., e.g., below 35° C.

The chamber 20 is also coupled to a chemical delivery system 30. The chemical delivery system 30 includes three or more gas sources 32a, 32b, 32c coupled by respective delivery tubes 34a, 34b, 34c and controllable valves 36a, 36b, 36c to the vacuum chamber 20. The chemical delivery system 30 can include a combination of restrictors, gas flow controllers, pressure transducers, and ultrasonic flow meters to provide a controllable flow rate of the various gasses into the chamber 20. The chemical delivery system 30 can also include one or more temperature control components, e.g., a heat exchanger, resistive heater, heat lamp, etc., to heat or cool the various gasses before they flow into the chamber 20. Although FIG. 1 illustrates separate gas lines extending in parallel to the chamber for each gas source, two or more of the gas lines could be joined, e.g., by one or more three-way valves, before the combined line reaches the chamber 20. In addition, although FIG. 1 illustrates three gas sources, the use of four gas sources could enable the in-situ formation of laminate structures having alternating layers of two different metal oxides.

Two of the gas sources provide two chemically different gaseous reactants for the coating process to the chamber 20. For example, the first gas source 32a can provide gaseous silicon tetrachloride ($SiCl_4$), whereas the second gas source 32b can provide water vapor.

One of the gas sources can provide a purge gas. In particular, the third gas source can provide a gas that is chemically inert to the reactants, the coating, and the particles being processed. For example, the purge gas can be $N_2$, or a noble gas, such as argon.

A rotatable coating drum 40 is held inside the chamber 20. The drum 40 can be connected by a drive shaft 42 that extends through a sealed port in a side wall of the chamber 20 to a motor 44. The motor 44 can rotate the drum at speeds of 1 to 100 rpm. Alternatively, the drum can be directly connected to a vacuum source through a rotary union.

The particles to be coated, shown as a particle bed 50, are placed in an interior volume 46 of the drum 40. The drum 40 and chamber 20 can include sealable ports (not illustrated) to permit the particles to be placed into and removed from the drum 40.

The body of the drum 40 is provided by one or more of a porous material, a solid metal, and a perforated metal. The pores through the cylindrical side walls of the drum 40 can have a dimension of 10 μm or less.

In operation, one of the gasses flows into chamber 20 from the chemical delivery system 30 as the drum 40 rotates. A combination of pores (0.1-100 μm), holes (0.1-10 mm), or large openings in the coating drum serves to confine the particles in the coating drum while allowing rapid delivery of precursor chemistry and pumping of byproducts or unreacted species. Due to the pores in the drum 40, the gas can flow between the exterior of the drum 40, i.e., the reactor chamber 20, and the interior of the drum 40. In addition, rotation of the drum 40 agitates the particles to keep them separate, ensuring a large surface area of the particles remains exposed. This permits fast, uniform interaction of the particle surface with the process gas.

In some implementations, one or more temperature control components are integrated into the drum 40 to permit control of the temperature of the drum 40. For example, resistive heater, a thermoelectric cooler, or other components can be integrated in or on the side walls of the drum 40.

The reactor system 10 also includes a controller 60 coupled to the various controllable components, e.g., vacuum pump 24, gas distribution system 30, motor 44, a temperature control system, etc., to control operation of the reactor system 10. The controller 60 can also be coupled to various sensors, e.g., pressure sensors, flow meters, etc., to provide closed loop control of the pressure of the gasses in the chamber 20.

In general, the controller 60 can operate the reactor system 10 in accord with a "recipe." The recipe specifies an operating value for each controllable element as a function of time. For example, the recipe can specify the times during which the vacuum pump 24 is to operate, the times of and flow rate for each gas source 32a, 32b, 32c, the rotation rate of the motor 44, etc.

The controller 60 can receive the recipe as computer-readable data (e.g., that is stored on a non-transitory computer readable medium).

The controller 60 and other computing devices part of systems described herein can be implemented in digital electronic circuitry, or in computer software, firmware, or hardware. For example, the controller can include a processor to execute a computer program as stored in a computer program product, e.g., in a non-transitory machine readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 60 is a general purpose programmable computer. In some implementations, the controller can be implemented using special purpose logic circuitry, e.g., an FPGA (field programmable gate array) or an ASIC (application specific integrated circuit).

Operation

The operation is illustrated with a process for providing a silicon oxide coating, but the operation is similar for ALD, MLD, or hybrid method. Initially, particles are loaded into the drum 40 in the reactor system 10. The particles can be an API, a solid dispersion of an API and one or more excipients, a mixture of two or more APIs or a mixture of one or more APIs or a mixture of one or more excipients. Once any access ports are sealed, the controller 60 operates the reactor system 10 according to the following recipe in order to form the thin-film oxide layers on the particles.

40 can be rotated during specific steps or during all steps.

In one embodiment, the controller 60 can operate the reactor system 10 as follows.

In a first reactant half-cycle, while the motor 44 rotates the drum 40 is to agitate the particles 50:
 i) The gas distribution system 30 is operated to flow the first reactant gas, e.g., SiCl$_4$, from the source 32a into the chamber 20 until a first specified pressure is achieved. The specified pressure can be 2 Torr to half of the saturation pressure of the reactant gas (e.g., for SiCl$_4$, about 170-200 torr).
 ii) Flow of the first reactant is halted, and a specified delay time (e.g., 1-30 minutes or 5-10 minutes) is permitted to pass, e.g., as measured by a timer in the controller. This permits the first reactant to flow through the particle bed in the drum 40 and react with the surface of the particles 50 inside the drum 40.
 iii) The vacuum pump 50 evacuates the chamber 20, e.g., down to pressures below 1 Torr, e.g., to 1 to 100 mTorr, e.g., 50 mTorr.

These steps (i)-(iii) can be repeated a number of times set by the recipe, e.g., two to ten times, e.g., six times.

Next, in a first purge cycle, while the motor 44 rotates the drum 40 to agitate the particles 50:
 iv) The gas distribution system 30 is operated to flow the inert gas, e.g., N$_2$, from the source 32c into the chamber 20 until a second specified pressure is achieved. The second specified pressure can be 1 to 20 Torr.
 v) Flow of the inert gas is halted, and a specified delay time is permitted to pass, e.g., as measured by the timer in the controller. This permits the inert gas to flow through the pores in the drum 40 and diffuse through the particles 50 to displace the reactant gas and any vaporous by-products.
 vi) The vacuum pump 50 evacuates the chamber 20, e.g., down to pressures below 1 Torr, e.g., to 1 to 500 mTorr, e.g., 50 mTorr.

These steps (iv)-(vi) can be repeated a number of times set by the recipe, e.g., six to twenty times, e.g., sixteen times.

In a second reactant half-cycle, while the motor 44 rotates the drum 40 agitates the particles 50 as follows:
 vii) The gas distribution system 30 is operated to flow the second reactant gas, e.g., H$_2$O, from the source 32a into the chamber 20 until a third specified pressure is achieved. The third pressure can be 2 Torr to 20 Torr.
 viii) Flow of the second reactant, e.g., H$_2$O, is halted and a specified delay time (e.g., 1-30 minutes or 5-10 minutes) is permitted to pass, e.g., as measured by the timer in the controller. This permits the second reactant to flow through the pores in the drum 40 and react with the surface of the particles 50 inside the drum 40.
 ix) The vacuum pump 50 evacuates the chamber 20, e.g., down to pressures below 1 Torr, e.g., to 1 to 500 mTorr, e.g., 50 mTorr.

These steps (vii)-(ix) can be repeated a number of times set by the recipe, e.g., two to ten times, e.g., six times.

Next, in a second (optional) purge cycle, while the motor 44 rotates the drum 40 is to agitate the particles 50 as follows:
 x) The gas distribution system 30 is operated to flow the inert gas, e.g., N$_2$, from the source 32c into the chamber 20 until a second specified pressure is achieved. The second specified pressure can be 1 to 20 Torr.
 xi) Flow of the inert gas is halted, and a specified delay time is permitted to pass, e.g., as measured by the timer in the controller 60. This permits the inert gas to flow through the pores in the drum 40 and diffuse through the particles 50 to displace the reactant gas and any vaporous by-products.
 xii) The vacuum pump 24 evacuates the chamber 20, e.g., down to pressures below 1 Torr, e.g., to 1 to 500 mTorr, e.g., 50 mTorr.

These optional steps (x)-(xii) can be repeated a number of times set by the recipe, e.g., six to twenty times, e.g., sixteen times.

This second purge cycle can be identical to the first purge cycle, or can have a different number of repetitions of the steps (x)-(xii) and/or different delay time and/or different pressure. The cycle of the first reactant half-cycle, first purge cycle, second reactant half cycle and second purge cycle can be repeated a number of times set by the recipe, e.g., 1 to 100 times.

As noted above, the inert gas purge after the second (water) half cycle is optional. It is been discovered that, for hydrophobic particles, e.g., hydrophobic APIs, it is not desirable to include an inert gas purge after the water half-cycle. Instead, the chamber can be pumped down to a pressure below 0.5 Torr, e.g., to between 0.1 Torr to 0.3 Torr, or to 0.050 Torr. In this way some residual water vapor remains in the chamber. The SiCl$_4$ is then flowed in to initiate the first reactant half-cycle and the residual moisture in the chamber allows the reaction to initiate on the API surface and proceed at a lower temperature. This process can be repeated 1 to 100 times, 1 to 10 times, to create a desired coverage of coating. Then the process can resume the normal purging process to reach the target coating thickness.

Thus, in some cases, the inert purge gas is not used after the first or first and second water half cycle, but is used after subsequent water half cycles.

As noted above, the coating process can be performed at a low processing temperature, e.g., below 100° C. or below 50° C., e.g., between 50° C. and 20° C. or between 45° C. and 20° C. In particular, the particles can remain or be maintained at such temperatures during all of the steps (i)-(ix) noted above. In general, the temperature of the interior of the reactor chamber does not exceed 35° C. during the steps (i)-(xii). This can be achieved by having the first reactant gas, second reactant gas and inert gas be injected into the chamber 20 at such temperatures during the respective cycles. In addition, physical components of the chamber 20 can remain or be maintained at such temperatures, e.g., using a cooling system, e.g., a thermoelectric cooler, if necessary.

Process for Preparing Pharmaceutical Compositions Comprising Drugs Encapsulated by One or More Layers of Silicon Oxide Provided are two exemplary methods for a pharmaceutical composition comprising a drug-containing core enclosed by one or more metal oxide materials. The first exemplary method includes the sequential steps of: (a) loading the particles comprising the drug into a reactor, (b) applying a vaporous or gaseous $SiCl_4$ to the substrate in the reactor, (c) performing one or more pump-purge cycles of the reactor using inert gas, (d) applying a vaporous or gaseous $H_2O$ to the substrate in the reactor, and (e) performing one or more pump-purge cycles of the reactor using inert gas. In some embodiments of the first exemplary method, the sequential steps (b)-(e) are optionally repeated one or more times to increase the total thickness of the one or more silicon oxide materials that enclose the solid core of the coated particles. In some embodiments, the reactor pressure is allowed to stabilize following step (a), step (b), and/or step (d). In some embodiments, the reactor contents are agitated prior to and/or during step (b), step (c), and/or step (e). In some embodiments, the reactor contents are agitated throughout the coating process. In some embodiments, a subset of vapor or gaseous content is pumped out prior to step (c) and/or step (e).

The second exemplary method includes (e.g., consists of) the sequential steps of (a) loading the particles comprising the drug into a reactor, (b) reducing the reactor pressure to less than 50 mTorr, (c) pressurizing the reactor by adding vaporous or gaseous $SiCl_4$, (d) allowing the reactor pressure to stabilize, (e) agitating the reactor contents, (f) pumping out a subset of vapor or gaseous content and determining when to stop pumping based on analysis of content in the reactor including precursor and byproduct of precursor reacting with exposed hydroxyl residues on substrate or on particle surface, (g) performing a sequence of pump-purge cycles of the reactor using insert gas, (h) pressuring the reactor by adding a vaporous or gaseous $H_2O$, (j) allowing the reactor pressure to stabilize, (k) agitating the reactor contents, (l) pumping out a subset of vapor or gaseous content and determining when to stop pumping based on analysis of content in reactor including precursor, byproduct of precursor reacting with exposed hydroxyl residues on substrate or on particle surface, and unreacted oxidant, and optionally, (m) performing a sequence of pump-purge cycles of the reactor using insert gas. In some embodiments of the second exemplary method, the sequential steps (b)-(m) are optionally repeated one or more times to increase the total thickness of the one or more metal oxide materials that enclose the solid core of the coated particles.

Pharmaceutically Acceptable Excipients, Diluents, and Carriers

Pharmaceutically acceptable excipients include, but are not limited to:

(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, carbomer and their polymers, emulsifiers, sugar gum, starch, organic acids and their salts, vinyl pyrrolidone and vinyl acetate;

(2) binding agents such as cellulose, cross-linked polyvinylpyrrolidone, microcrystalline cellulose;

(3) filling agents such as lactose monohydrate, lactose anhydrous, microcrystalline cellulose and various starches;

(4) lubricating agents such as agents that act on the flowability of a powder to be compressed, including colloidal silicon dioxide, talc, stearic acid, magnesium stearate, calcium stearate, silica gel;

(5) sweeteners such as any natural or artificial sweetener including sucrose, xylitol, sodium saccharin, cyclamate, aspartame, and acesulfame K;

(6) flavoring agents;

(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quaternary compounds such as benzalkonium chloride;

(8) buffers;

(9) Diluents such as pharmaceutically acceptable inert fillers, such as microcrystalline cellulose, lactose, dibasic calcium phosphate, saccharides, and/or mixtures of any of the foregoing;

(10) wetting agents such as corn starch, potato starch, maize starch, and modified starches, and mixtures thereof;

(11) disintegrants; such as croscarmellose sodium, crospovidone, sodium starch glycolate; and

(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate)

EXAMPLES

Example 1: Prepare Particles Comprising Drug Encapsulated by Metal Oxide and Polymer Layers In this Example, one of the methods disclosed for preparing silicon oxide coated particles comprising an API was performed and the data is presented. The vaporous or gaseous precursor is $SiCl_4$, the byproduct gaseous HCl formed after $SiCl_4$ reacts with exposed hydroxyl groups on the particles or on surface of the coated particles, and the oxidant is $H_2O$.

Method for Silicon Oxide Coating

In brief, the method comprised the sequential steps of:

(a) loading particles comprising the drug into a reactor;

hydrophobic (Log P 3.7), better results were achieved with a higher $SiCl_4$ pressure and no $N_2$ purge (100 mTorr $H_2O$ at end of each $H_2O$).

TABLE 1

| Sample | Process Conditions<br>Cycle pressure - Torr (hold time - min) | TGA (wt %) | Thickness by TGA (nm) | FF |
|---|---|---|---|---|
| APAP-1 | 100 (30) $SiCl_4$: 8 (30) $H_2O$ - 19 cycles ($N_2$ purge after $H_2O$) | 4.43% | 15 | 7 |
| APAP-2 | 5 (10) $SiCl_4$: 5 (10) $H_2O$ - 80 cycles ($N_2$ purge after $H_2O$) | 2.48% | 32 | 3.57 |
| APAP-3 | 40 (10) $SiCl_4$: 8(10) $H_2O$ - 15 cycles (no $N_2$ purge after $H_2O$; brought to 0.5 Torr) | 1.29% | 15 | 2.3 |
| THEO-1 | 175 (30) $SiCl_4$: 15 (30) $H_2O$ - 10 cycles ($N_2$ purge after $H_2O$) | — | 2.5 | 19.4 |
| THEO-2 | 100 (30) $SiCl_4$: 8(30) $H_2O$ - 25 cycles ($N_2$ purge after $H_2O$) | — | 5 | 15.9 |
| THEO-3 | 20 (10) $SiCl_4$: 8(10) $H_2O$ - 30 cycles (no $N_2$ purge after $H_2O$, 0.1 Torr) | — | 17 | 13.2 |
| IBU-1 | 100 (10) $SiCl_4$: 8 (10) $H_2O$ - 15 cycles ($N_2$ purge after $H_2O$) | 0.96% | 6.7 | 6.6 |
| IBU-2 | 40 (10) $SiCl_4$: 8(10) $H_2O$ - 45 cycles ($N_2$ purge after $H_2O$) | 0.86% | 16.5 | 5.82 |
| IBU-3 | 40 (10) $SiCl_4$: 8 (10) $H_2O$ - 7 cycles (no $N_2$ purge after $H_2O$, 0.3 Torr) | 0.25% | — | 4.25 |
| IBU-4 | 20 (10) $SiCl_4$: 8(10) $H_2O$ - 30 cycles (no $N_2$ purge gas after $H_2O$, 0.1 Torr) | 0.31% | 10 | 9.95 |

(b) reducing the reactor pressure to less than 1 Torr (e.g., below 50 mtorr);

(c) pressurizing the reactor to at least 1 Torr by adding a vaporous or gaseous $SiCl_4$;

(d) allowing the reactor pressure to stabilize;

(e) pumping out a subset of vapor or gaseous content, including gaseous HCl and unreacted $SiCl_4$, and determining when to stop pumping by performing RGA to monitor levels of gaseous HCl and unreacted $SiCl_4$ in the reactor.

(f) performing a sequence of pump-purge cycles on the reactor using nitrogen gas;

(g) pressuring the reactor to at least 1 Torr by adding water vapor;

(h) allowing the reactor pressure to stabilize;

(i) pumping out a portion of vapor or gaseous content, including HCl, water vapor, and determining when to stop pumping by performing RGA to monitor levels of water vapor in the reactor; and, in some cases, (j) performing a sequence of pump-purge cycles on the reactor using nitrogen gas.

Additionally, the steps of (b)-(i) were repeated more than once to increase the total thickness of the silicon oxide that encloses the drug particle core.

Figure 2:
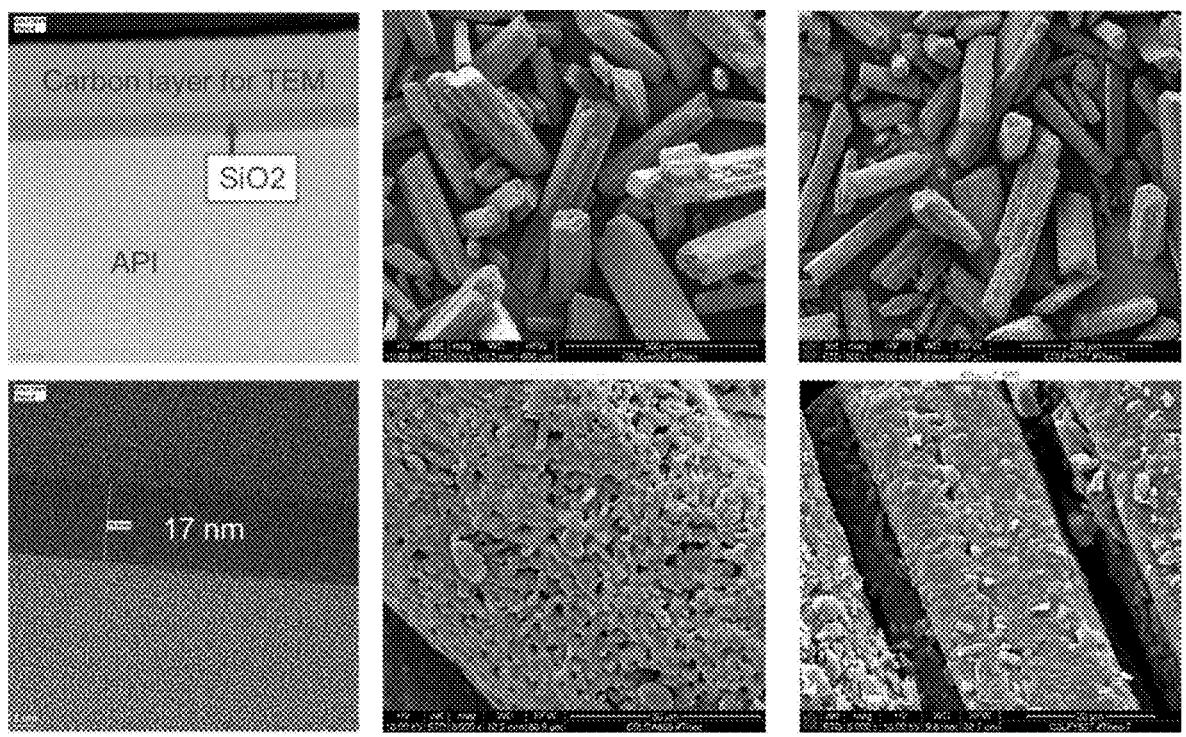
FIG. 2 is a series of images of theophylline particles. The panels at the left are TEM cross sections of particles coated with silicon oxide as described above. The center panels are SEM images of the uncoated particles, and the panels at the right are SEM images of the coated particles.

Three different APIs were coated with silicon oxide. Table 1 summarizes the reaction conditions and results. Acetaminophen (APAP) and theophylline (THEO) are hydrophilic (Log P 0.46 and −0.02, respectively). Flowability (Flow Function; "FF") of the uncoated APAP particles was 2.61. Flowability of the uncoated THEO particles was 10. As can be seen in Table 1, for these APIs better results were achieved with a $N_2$ purge after the water cycle. Without being bound by any theory, it may be that in the absence of a purge, residual water vapor causes deposition that is too rapid to yield improved flowability. In addition, poor flowability might be caused by excess moisture in coated powder. In contrast, ibuprofen (uncoated FF 4.23), which is FIG. 2 is a series of images of theophylline particles. The panels at the left are TEM cross sections of particles coated with silicon oxide as described above. The center panels are SEM images of the uncoated particles, and the panels at the right are SEM images of the coated particles.

Figure 3:
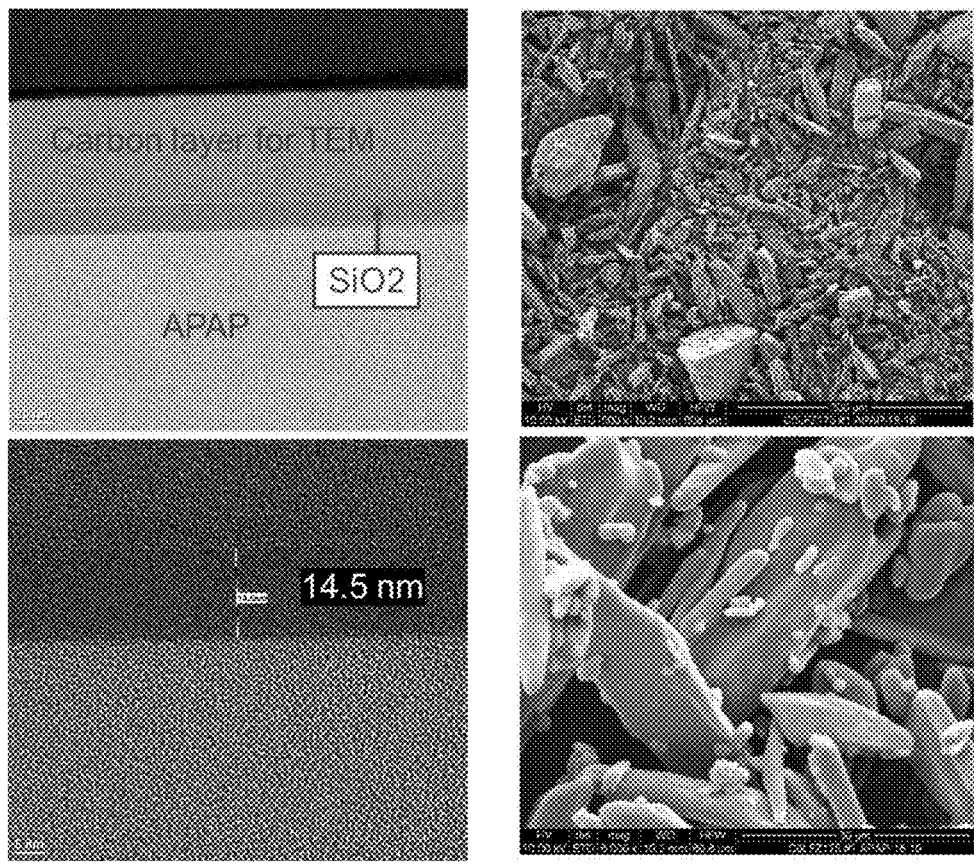
FIG. 3 is a series of images of acetaminophen particles. The panels at the left are TEM cross sections of particles coated with silicon oxide as described above. The panels at the right are SEM images of the coated particles.

FIG. 3 is a series of images of acetaminophen particles. The panels at the left are TEM cross sections of particles coated with silicon oxide as described above. The panels at the right are SEM images of the coated particles.

Figure 4:
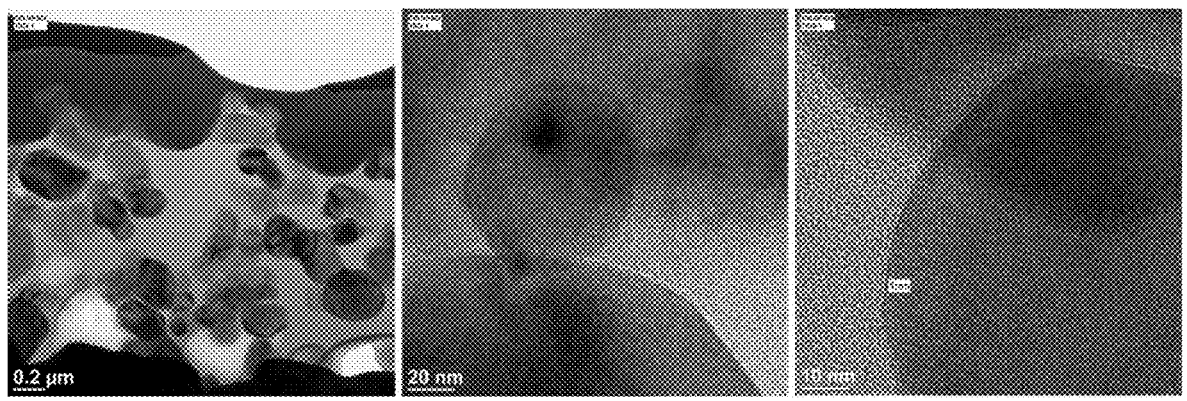
FIG. 4 is a series of images of $TiO_2$ particles coated with silicon oxide as described above.

FIG. 4 is a series of images of $TiO_2$ particles coated with silicon oxide as described above.

Figure 5:
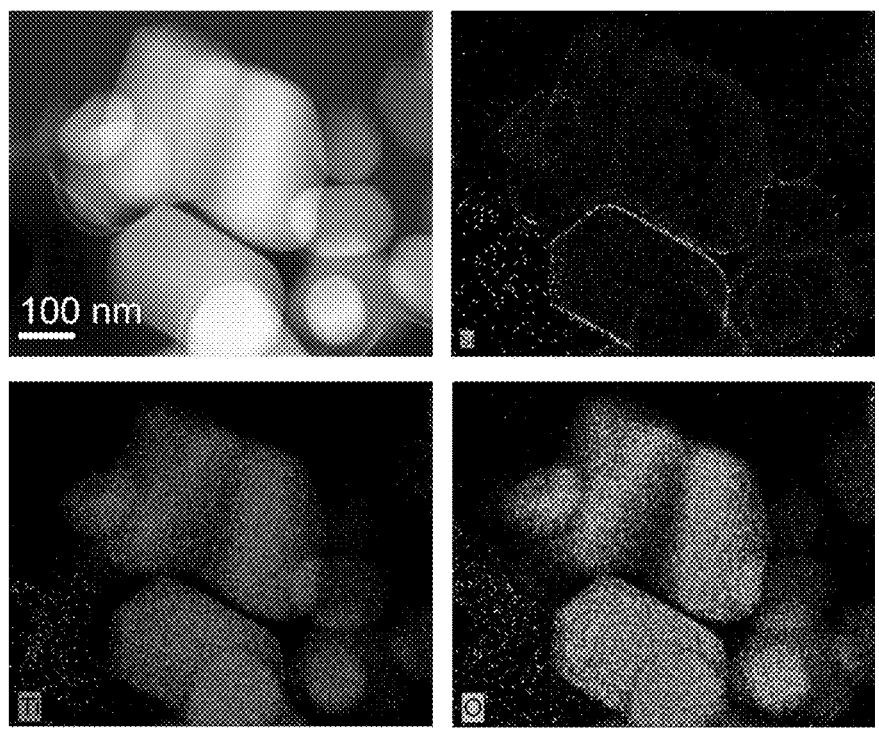
FIG. 5 is a series of images of EDS mapping of $TiO_2$ particles coated with silicon oxide as described above.

FIG. 5 is a series of images of EDS mapping of $TiO_2$ particles coated with silicon oxide as described above. Conformal coating of SiO2 on a TiO2 particle is shown by the EDS mapping.

What is claimed is:

1. A method of preparing coated particles comprising an active pharmaceutical ingredient (API)-containing core enclosed by one or more silicon oxide layers, the method comprising:
   (a1) loading particles comprising a hydrophobic API into a reactor;
   (a2) applying gaseous $SiCl_4$ to the particles in the reactor;
   (a3) performing one or more pump-purge cycles using inert gas;
   (a4) applying gaseous $H_2O$ to the particles in the reactor; and
   (a5) lowering the gaseous $H_2O$ pressure in the reactor to below 0.5 Torr,
   (b) performing two or more reaction cycles, each reaction cycle consisting of steps (a2)-(a5), to increase the total thickness of the silicon oxide layer, thereby creating coated particles comprising an API-containing core, wherein reaction cycles take place between 25° C. and 50° C. in the absence of a catalyst, and there is no pump-purge cycle between the first and second reaction cycles.

2. The method of claim 1, wherein there is no pump-purge cycle between the second and the third reaction cycles.

3. The method of claim 1, wherein there is no pump-purge cycle between any of the first 10 reaction cycles.

4. The method of claim 1, wherein there is no pump-purge cycle between any of the first 100 reaction cycles.

5. The method of claim 1, wherein the particles are agitated prior to and/or during one or more of steps (a2) to (a5).

6. The method of claim 1, wherein the particles are agitated prior to and/or during step (a1), step (a3), and/or step (a5).

7. The method of claim 1, wherein a subset of gaseous $SiCl_4$ is pumped out prior to step (a3).

8. The method of claim 1, wherein the silicon oxide layer has a thickness in a range of 0.1 nm to 50 nm.

9. The method of claim 1, wherein the particles are not removed from the reactor between the reaction cycles.

10. The method of claim 1, wherein the particles are not removed from the reactor during step until the silicon oxide layer is complete.

11. The method of claim 1, wherein the API-containing core comprises one or more pharmaceutically acceptable excipients.

12. The method of claim 1, wherein the particles in step (a1) have a median particle size, on a volume average basis between 0.1 μm and 20 μm.

13. The method of claim 1, wherein the particles in step (a1) have a median particle size, on a volume average basis between 0.1 μm and 5 μm.

14. The method of claim 1, wherein the particles in step (a1) have a median particle size, on a volume average basis between 0.1 μm and 1000 μm.

15. The method of claim 1, wherein the API-containing core comprises the hydrophobic API and a second API.

16. The method of claim 1, wherein the API-containing core consists of the hydrophobic API.

17. The method of claim 1, wherein the API-containing core consists of the hydrophobic API and a second API.

18. The method of claim 1, wherein the API-containing core comprises the hydrophobic API, a second API and one or more pharmaceutically acceptable excipients.

19. The method of claim 1, wherein the API-containing core consists of the hydrophobic API and one or more pharmaceutically acceptable excipients.

20. The method of claim 1, wherein the API-containing core consists of the hydrophobic API, a second API and one or more pharmaceutically acceptable excipients.

21. The method of claim 1, wherein the API-containing core comprises the hydrophobic API and step (a1) further comprises one or both of (1) loading particles comprising a second API into the reactor (second particles) and (2) loading particles comprising one more excipients into the reactor (excipient particles).

22. The method of claim 1, further comprising admixing the coated particles with a pharmaceutically acceptable diluent or carrier.

23. The method of claim 1, further comprising processing the coated particles to form a tablet or capsule.

24. The method of claim 1, further comprising admixing the coated particles with a pharmaceutically acceptable diluent or carrier to form a mixture and processing the mixture to form a table or capsule.

25. The method of claim 1, wherein each pump-purge cycle comprises flowing an inert gas into the reactor to reach a pressure of at least 1 Torr and after a delay time evacuating the reactor to reduce the pressure of the inert gas to below 1 Torr.

26. The method of claim 1, wherein the gaseous $SiCl_4$ is pumped into the reactor to reach a pressure of 2 to 200 Torr during step (a2).

27. The method of claim 1, wherein step (a3) is the only pump-purge step.

28. The method of claim 1, wherein the gaseous $H_2O$ is pumped into the reactor to reach a pressure of 2 to 20 Torr and is allowed to react with $SiCl_4$ in the reactor for 1-30 minutes during step (a4).

29. The method of claim 1, wherein there is one or more pump-purge cycles between the second and each subsequent cycles.

30. The method of claim 1, wherein there is one or more pump-purge cycles between the third and each subsequent cycles.

31. The method of claim 1, wherein there is one or more pump-purge cycles between the 10th and each subsequent cycles.

32. The method of claim 1, wherein there is one or more pump-purge cycles between the 100th and each subsequent cycles.

* * * * *

UNITED STATES PATENT AND TRADEMARK OFFICE
CERTIFICATE OF CORRECTION

| | | |
|---|---|---|
| PATENT NO. | : 12,064,522 B2 | Page 1 of 1 |
| APPLICATION NO. | : 17/492363 | |
| DATED | : August 20, 2024 | |
| INVENTOR(S) | : Fei Wang et al. | |

It is certified that error appears in the above-identified patent and that said Letters Patent is hereby corrected as shown below:

In the Claims

In Column 14, Line 5, Claim 21, delete "one more" and insert -- one or more --.

In Column 14, Line 15, Claim 24, delete "table" and insert -- tablet --.

Signed and Sealed this
Eighth Day of October, 2024

Katherine Kelly Vidal
*Director of the United States Patent and Trademark Office*